(12) United States Patent
Kuzma

(10) Patent No.: US 7,174,218 B1
(45) Date of Patent: Feb. 6, 2007

(54) LEAD EXTENSION SYSTEM FOR USE WITH A MICROSTIMULATOR

(75) Inventor: Janusz A Kuzma, Parker, CO (US)

(73) Assignee: Advanced Bionics Corporation, Valencia, CA (US)

( * ) Notice: Subject to any disclaimer, the term of this patent is extended or adjusted under 35 U.S.C. 154(b) by 7 days.

(21) Appl. No.: 10/915,979

(22) Filed: Aug. 11, 2004

Related U.S. Application Data (60) Provisional application No. 60/494,443, filed on Aug. 12, 2003.

(51) Int. Cl.
*A61N 1/05* (2006.01)
(52) U.S. Cl. .................................... 607/116; 439/909
(58) Field of Classification Search ............... 607/115, 607/3, 116, 2, 37; 439/909
See application file for complete search history.

(56) References Cited

U.S. PATENT DOCUMENTS

| | | | |
|---|---|---|---|
| 5,324,316 A | | 6/1994 | Schulman et al. |
| 5,405,367 A | | 4/1995 | Schulman et al. |
| 6,051,017 A | | 4/2000 | Loeb et al. |
| 6,175,764 B1 | * | 1/2001 | Loeb et al. ............... 607/3 |
| 6,738,672 B2 | | 5/2004 | Schulman et al. |

FOREIGN PATENT DOCUMENTS

| WO | WO 98/37926 | 9/1998 |
|---|---|---|
| WO | WO 98/43700 | 10/1998 |
| WO | WO 98/43701 | 10/1998 |
| WO | WO 03/063951 A1 | 8/2003 |

OTHER PUBLICATIONS

Whitehurst, et al. Inventors for AB-203U; U.S. Appl. No. 10/178,011; filed Jun. 20, 2002; entitled "Implantable Microstimulators with Programmable Multielectrode Configuration and Uses Thereof".

Kuzma inventor for AB-057U1; U.S. Appl. No. 10/188,465; filed Jul. 2, 2002; entitled "Implantable Microdevice with Extended Lead and Remote Secondary Coil".

* cited by examiner

*Primary Examiner*—Jeffrey R Jastrzab
(74) *Attorney, Agent, or Firm*—Philip H. Lee (57) ABSTRACT

An adapter system is provided for adapting and connecting a leadless microstimulator to a separate monopolar, bipolar, or tripolar electrode. Advantageously, the microstimulator does not need to be physically modified. The adapter system encloses the microstimulator and electrically connects the microstimulator to the selected, separate electrode via an extension lead or leads. The adapter has two forms: a monopolar adapter having a single opening or a bipolar adapter having two openings. The separate electrode is equipped with at least one extension lead having a connector that can be inserted into the opening of the monopolar adapter or the bipolar adapter and connect to the microstimulator that is placed within the monopolar or bipolar adapter.

20 Claims, 8 Drawing Sheets

LEAD EXTENSION SYSTEM FOR USE WITH A MICROSTIMULATOR

The present application claims the benefit of U.S. Provisional Patent Application Ser. No. 60/494,443, filed 12 Aug. 2003, which application is herein incorporated by reference in its entirety.

BACKGROUND OF THE INVENTION

The present invention relates to implantable electrical stimulation systems and, more particularly, relates to lead extension and adapter systems that may be used in conjunction with a leadless, implantable microstimulator.

A neurostimulator is a device that provides electrical stimulation to selected nerves in the body. One type of neurostimulator that has been developed in recent years is a tiny microstimulator known as a BION® microstimulator. Various embodiments and features of the BION microstimulator are disclosed, e.g., in U.S. Pat. Nos. 5,324,316; 5,405,367; 6,051,017; and in PCT Publications WO 98/37926; WO 98/43700 and WO 98/43701, each of which patents or publications are incorporated herein by reference.

A microstimulator may be implanted via a small incision and/or via endoscopic means. In one preferred embodiment, the microstimulator is leadless, having electrodes fashioned or formed into its case. A "lead" as used herein will refer to an elongate body that includes a conductor and an insulation covering the conductor. The lead can further include an electrode on one end of the lead and a connector on the other end of the lead. The term "electrode" will be used herein as that portion (including insulation portion) of a stimulating lead which contains an electrode contact or electrode contacts for delivering the electrical stimulation to a tissue.

A leadless microstimulator must be implanted next to the nerve or tissue that is to be stimulated, since the electrode contacts are placed directly on the microstimulator case. The small size of the microstimulator allows it to be placed through minimally invasive surgery.

In other applications, however, it is not possible to implant the microstimulator immediately next to the nerve or tissue to be stimulated. In such instances, a leaded BION microstimulator may be used. Some examples are shown in co-pending U.S. patent application Ser. No. 10/188,465, filed 2 Jul. 2002 and in U.S. patent application Ser. No. 10/178,011, filed 20 Jun. 2002. Both of these patent applications are incorporated herein by reference.

In some cases, a leadless microstimulator may need to be used for an application that requires a lead extension. In particular, use of a specific type of electrode may be desired because the electrode type and number of electrode contacts are optimized for a specific application.

One type of electrode known in the art is a cuff electrode. A cuff electrode encircles a target nerve fiber or bundle and offers the advantage of being effectively attached to the target fiber or bundle, which prevents the electrode from inadvertently moving away from the desired, target nerve. A variation of the cuff electrode is a semi-cuff electrode that wraps or contacts one side of a target nerve bundle. A semi-cuff electrode may have one or more electrode contacts and operate as a monopolar electrode, a bipolar electrode or as a tripolar electrode, among others.

It would be desirable, in certain applications, to use a leadless microstimulator and to connect this microstimulator to a specific type of leaded electrode, for instance, a tripolar, semi-cuff electrode.

What is needed, therefore, is a system for adapting a leadless microstimulator so that it may be used with an extension lead that is connected to a selected electrode, such as a tripolar, semi-cuff electrode.

SUMMARY OF THE INVENTION

The present invention addresses the above and other needs by providing a system that adapts a leadless microstimulator so that it may be used with an electrode having at least one or two extension leads.

In one aspect of the invention, there is provided a system for connecting a leadless, microstimulator to an electrode having at least one extension lead. The system includes a monopolar adapter, which has an inner, adapter chamber that is sized to accept placement of the microstimulator within the chamber. The adapter chamber opens to the outside of the monopolar adapter through an opening on one end of the adapter. An indifferent electrode is placed on the other end of the monopolar adapter. The system also includes an extension lead connector, which has a connector contact at the end of the extension lead. The other end of the extension lead is electrically connected to a stimulating electrode which has at least one electrode contact. The extension lead connector has at least one part that is dimensioned to be inserted into the opening of the adapter to thereby seal the adapter opening. With the extension lead connector thus placed into the adapter opening, the connector contact abuts against the microstimulator's cathode electrode contact. When the microstimulator is placed inside the adapter chamber, the indifferent contact within the adapter chamber abuts the microstimulator indifferent electrode.

The adapter chamber is preferably substantially cylindrical. In addition, the exterior profile or shape of the adapter is preferably substantially cylindrical, with exception of the end acting as an indifferent electrode. That end preferably has a smooth profile such as a bullet shape or some other curved shaped.

In one embodiment, one or more sealing rings are used to encircle the microstimulator when it is placed into the adapter chamber. The sealing ring or rings can be integrated into the inner wall of the adapter chamber and be made of exactly the same material as the adapter chamber wall.

To ensure proper long-term connection between the adapter and the extension lead connector, a connection system is provided. This connection system comprises a circular flange located on the extension lead connector. The monopolar adapter also has a circular recess inside the chamber, near the opening of the adapter which recess has a shape that is complementary to the circular flange. In operation, when the extension lead connector is inserted into the adapter opening, the flange snaps into the circular recess. As a further device to ensure that the extension lead connector cannot be easily pulled out from the adapter opening, the monopolar adapter may also have two sliding rings that slide along the exterior length of the adapter. The monopolar adapter may have a slightly larger exterior diameter (or circumference) at the opening end compared to the midportion of the adapter. By sliding the sliding ring towards the adapter opening and over the circular recess, the circular flange residing within the recess is placed under compression, thereby locking and sealing the connector within the opening of the monopolar adapter.

The use of this connection system in conjunction with an elastic adapter chamber wall also serves another important purpose. After the microstimulator has been inserted into the adapter chamber, the monopolar adapter is "pulled over" the connector. A "lip" placed at the very end of the adapter opening may be used to grasp the adapter during this step. This process of inserting the connector into the adapter opening stretches the monopolar adapter walls lengthwise so that, when the connector flange snaps into the adapter recess, the chamber walls are stretched slightly and therefore placed under elastic tension. This tension serves an important function because it keeps the microstimulator's indifferent electrode in compressive contact with the indifferent contact inside the adapter chamber and the microstimulator's cathode contact in compressive contact with the contact on the extension lead connector.

In another embodiment of the present invention, there is provided a system for connecting a leadless microstimulator to an electrode having at least two extension leads. The system includes a bipolar adapter, which has an inner, adapter chamber that is sized to accept placement of the microstimulator therein. The adapter has a first end and a second end. The bipolar adapter has a first opening on the first end and a second opening on the second end. The system also includes at least two extension lead connectors, each having a connector contact at the end. Each extension lead is electrically connected to at least one electrode contact and thus there are at least two electrode contacts in the stimulating electrode. Both extension lead connectors are preferably identical and have at least one part that is dimensioned to be inserted into either the first or second opening of the bipolar adapter. With an extension lead connector placed into one of the adapter openings, the connector contact is in contact with one of the electrode contacts of the microstimulator.

The adapter chamber within the bipolar adapter may be substantially cylindrical. In the preferred embodiment the adapter exterior shape can be substantially cylindrical along the length of the adapter from the first end to the second end.

The adapter may include at least one sealing ring, which ring is sized to encircle the microstimulator when it is placed in the adapter chamber. The sealing ring can be an integral part of the adapter chamber wall and may be made from the same material as the adapter chamber wall.

The adapter chamber can include a circular recess near both the first and second adapter openings. The lead connector of the extension lead can also have a circumferential flange that is complementary in shape to the circular recess and fits in the recess.

In one embodiment, the bipolar adapter includes a first and second sliding rings that encircle the exterior of the adapter. The sliding rings, preferably made from biocompatible metal, such as stainless steel or titanium, can slide along the exterior length of the adapter. The adapter may have an outer circumference that is slightly larger near the first and second ends of the adapter compared to the midportion of the adapter. When a sliding ring is advanced to the opening end, the ring squeezes and compresses the adapter wall and thereby locks the complementary flange into the circular recess.

Similar to the monopolar adapter, the chamber wall of the bipolar adapter will be under elastic tension when both first and second adapter openings have been plugged by lead connecters that are attached to extension leads. The elastic tension places the microstimulator's anode and cathode contacts in compressive contact with the two connector contacts.

It is thus a feature of the present invention to provide an adapter system that uses an existing leadless microstimulator without modifying the microstimulator. Various electrode configurations, including monopolar, bipolar and tripolar electrode configurations may be connected to the leadless microstimulator using the appropriate monopolar or bipolar adapter and one or more extension leads having a complementary connector that is insertable into the one or two openings of the monopolar or bipolar adapter.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
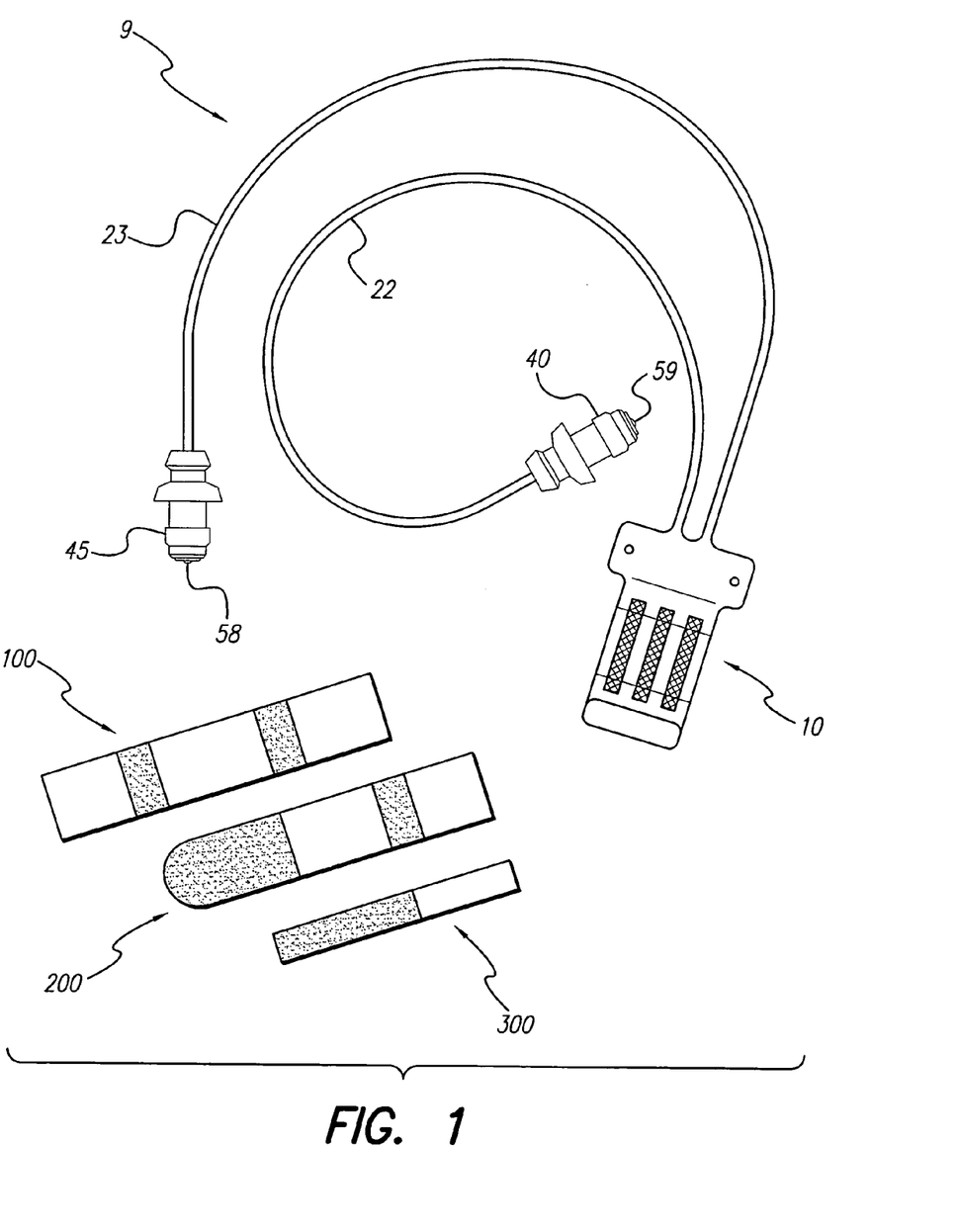
FIG. 1 shows, in accordance with the present invention, an illustration of the lead extension and adapter system which includes a microstimulator, a semi-cuff electrode with two extension leads and connectors, and bipolar and monopolar adapters.

FIG. 1 shows, in accordance with the present invention, an illustration of an adapter system 9 which illustration includes a microstimulator 300, a semi-cuff, tripolar electrode 10 with two extension leads 22 and 23 and lead connectors 40 and 45, connector contacts 59 and 58, respectively, and a bipolar adapter 100 and monopolar adapter 200.

Figure 2:
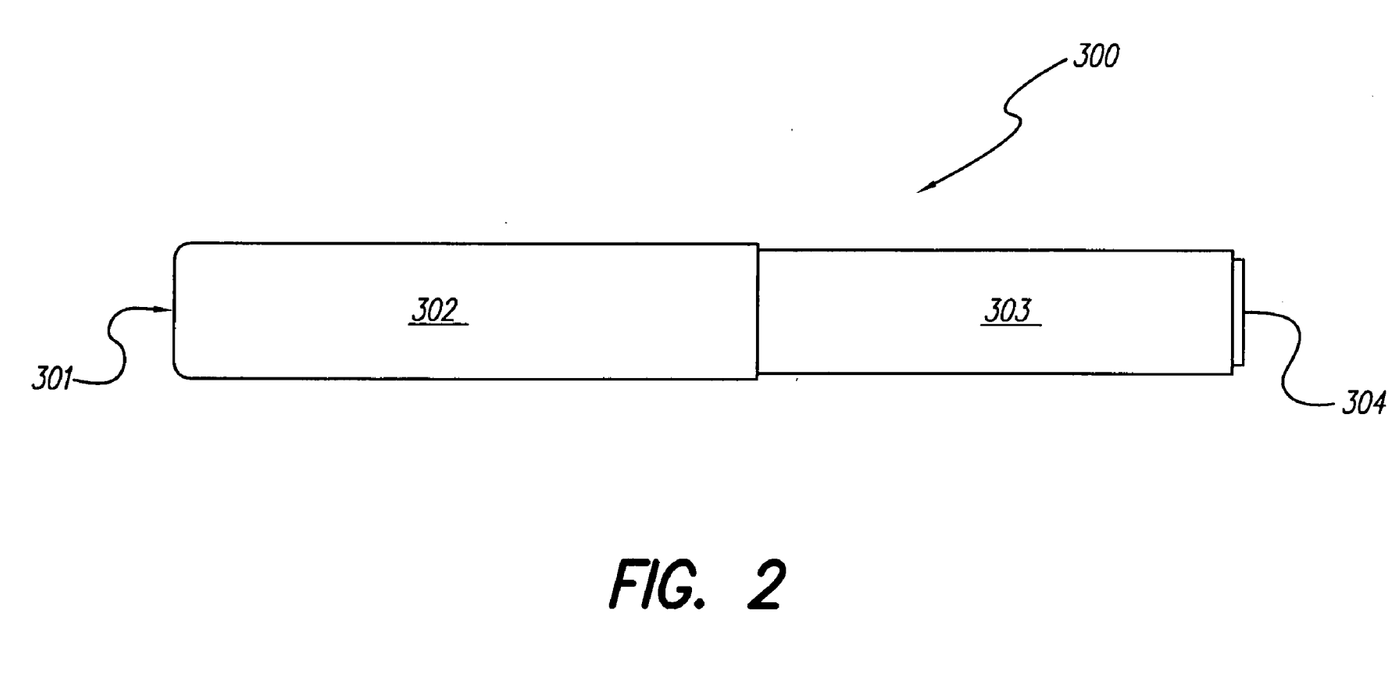
FIG. 2 shows, in accordance with the present invention, an illustration of an exemplary leadless microstimulator with two electrode contacts.

FIG. 2 shows a microstimulator 300 which has two electrode contacts: an anode (positive) contact 302 and a cathode (negative) contact 304. End 301 may be part of the anode contact. A non-metallic portion 303 of the microstimulator 300 may be made of a body inert material such as a ceramic.

Figure 3A:
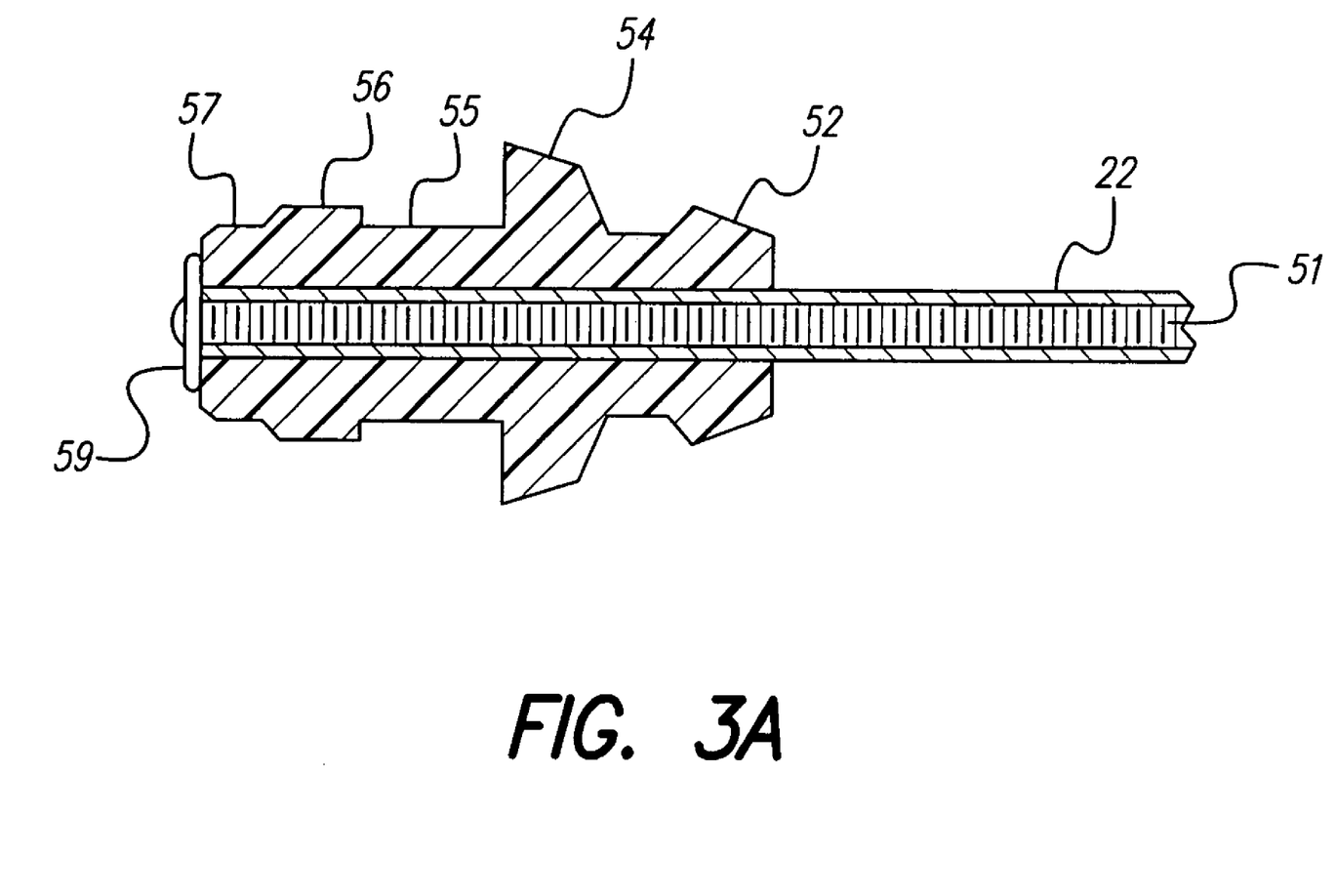
FIG. 3A shows, in accordance with the present invention, an illustration of a lead connector that can be attached to an extension lead which, in turn, can be connected to an electrode, such as a tripolar, semi-cuff electrode.

FIG. 3A shows, in accordance with the present invention, a cross-sectional view of lead connector 40 (identical to lead connector 45) that is attached to lead extension 22 (or lead extension 23) of the tripolar, semi-cuff electrode 10. The lead connector 40 has an electrode contact 59, an end portion 57 that is made of an insulating material, a circular flange 56 that has a diameter which is larger than the diameter of the end portion 57, a section 55 having a diameter (or circumference) that is approximately the same as the end portion 57, a stop 54, and a strain relief/grip 52 for grasping the end connector 40. A conductor 51 extends through the extension lead 22 and connects to the connector contact 59.

Figure 3B:
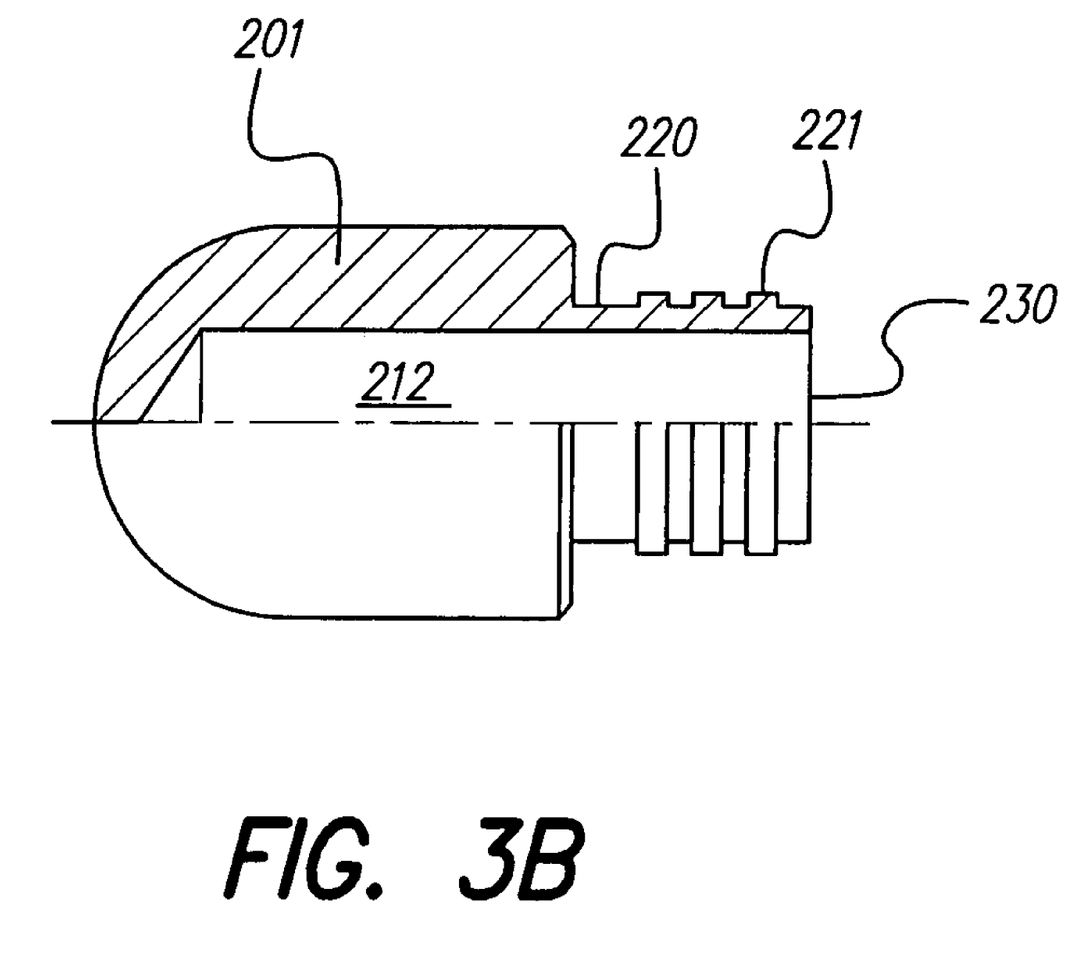
FIG. 3B shows, in accordance with the present invention, the indifferent electrode that is incorporated into a monopolar adapter.

FIG. 3B shows a partial, cross-sectional view of the indifferent electrode 201 alone. The indifferent electrode 201 has a hollowed out chamber that opens at end 230 and thereby forms part of the adapter chamber 212. The indifferent electrode also may have a thread portion 220 that has circular teeth, threads or ridges 221 that encircle the thread portion 220. The adapter body, which preferably is a stretchable insulation material such as silicone or polyurethane, may be stretched over the thread portion 220 to form the complete monopolar adapter.

Figure 4A:
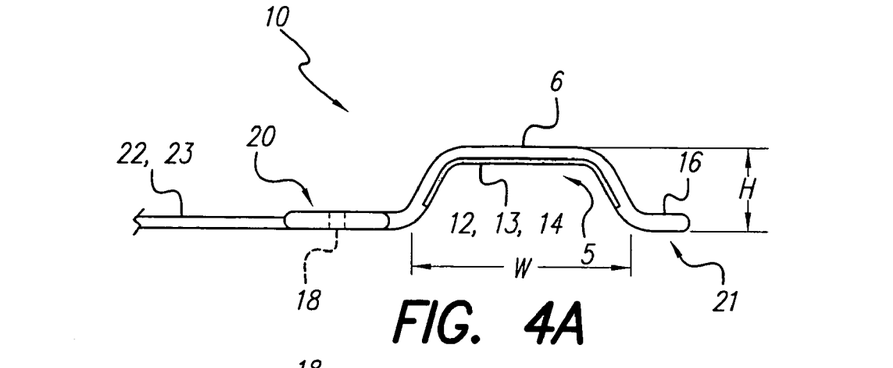
FIGS. 4A, 4B and 4C show an exemplary semi-cuff, tripolar electrode having three electrode contacts.
Figure 4B:
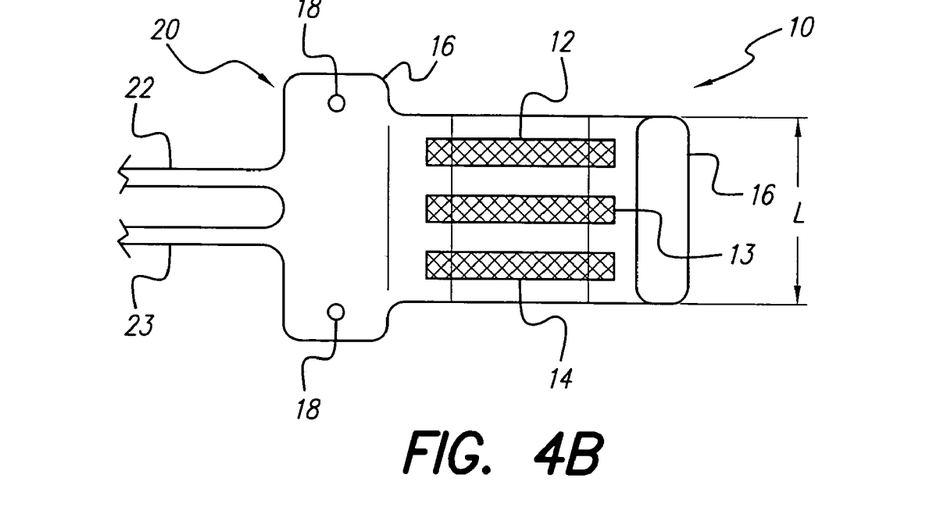
Figure 4C:
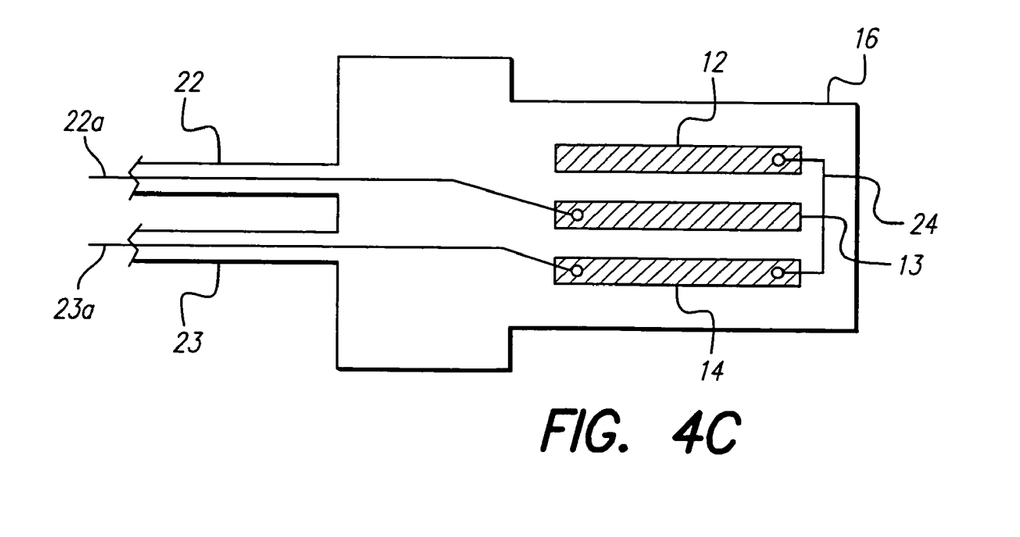

FIGS. 4A, 4B and 4C show various views of the tripolar, semi-cuff electrode 10. FIG. 4A shows a side view of the semi-cuff electrode. The view shows the trough 5 of the semi-cuff electrode wherein the electrode contacts 12, 13, and 14 are exposed. The trough has a depth H and width W. The semi-cuff electrode has a distal tip 16 and a proximal end 20. The electrode contacts are placed on a substrate of insulation 6 which may be, for instance, silicone or polyurethane. FIG. 4B shows a top view of the semi-cuff electrode, showing the three electrode contacts 12, 13 and 14 placed in parallel and suture holes 18. Lead extensions 22 and 23 are also shown. FIG. 4C shows a schematic view of the electrical connections between the electrode contacts 12, 13, and 14. In this example, electrode contacts 12 and 14 are connected via connection 24 and are further connected to conductor 23a in lead 23. Electrode contact 13 is connected to conductor 22a in lead 22. In this tripolar electrode arrangement, electrode contacts 12 and 14 are typically anodic (positive) while electrode contact 13 is the cathode (negative).

In order to deliver electrical current to the electrode contacts in the tripolar electrode connector, contacts 58 and 59 (as shown in FIG. 1) must be electrically connected to the microstimulator at its electrode contacts 301 and 304 (as shown in FIG. 2).

Figure 5:
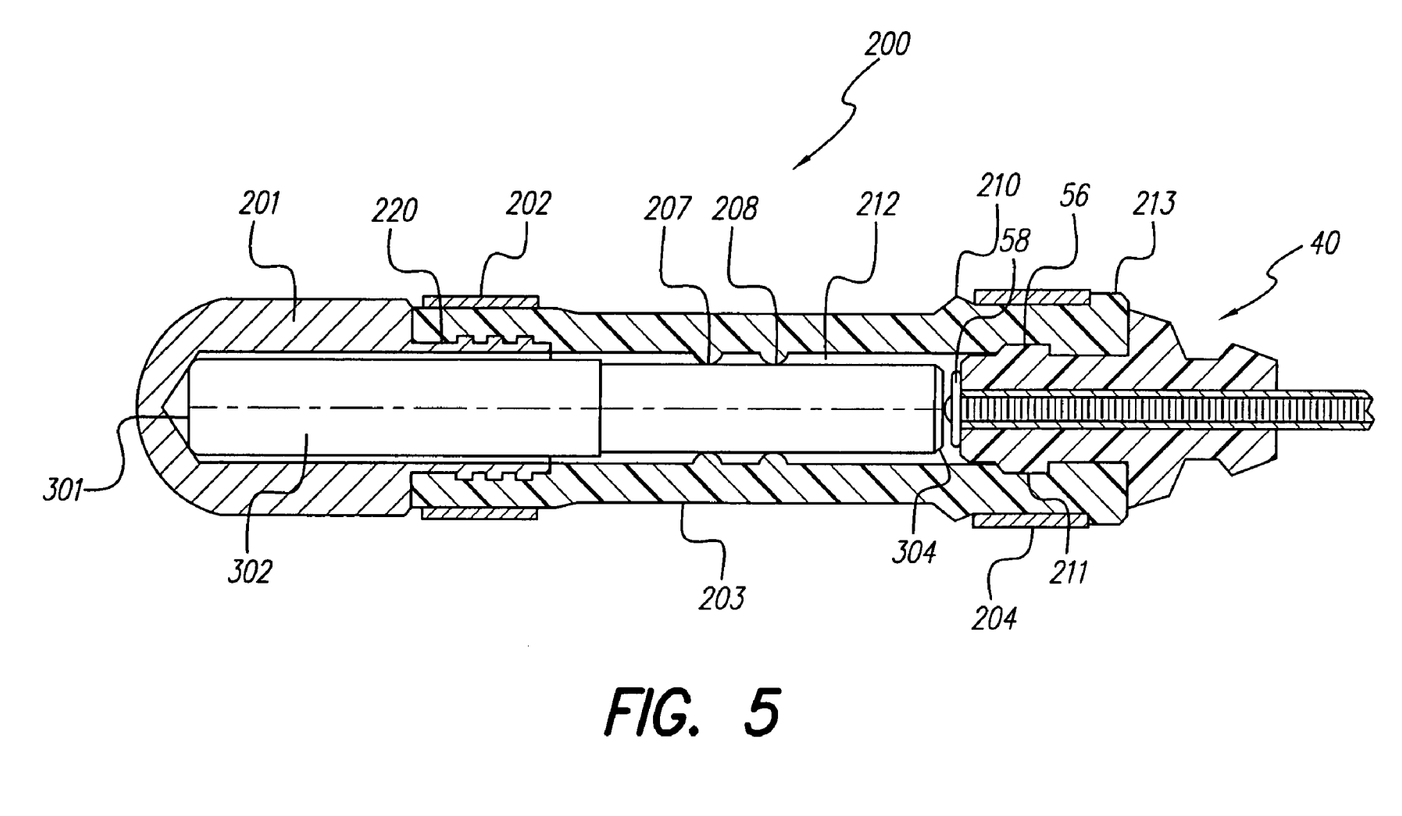
FIG. 5 shows, in accordance with the present invention, a monopolar adapter.

FIG. 5 shows, in accordance with the present invention, a cross-sectional, side view of the monopolar adapter 200 with the microstimulator inserted into the monopolar adapter chamber 212 and with the lead extension connector 40 inserted. The indifferent, anode contact 201 covers one end of the adapter 200. There is an opening at the other end of the adapter 200, into which a lead extension connector 40 or 45 may be interchangeably inserted.

If connector 45 is inserted into the adapter opening, only the middle electrode contact 13 in the tripolar electrode 10 will be connected. If the connector 40 is inserted into the adapter opening, then the two outer electrode contacts 12 and 14 in tripolar electrode 10 will be connected. Of course, other combinations of electrode contacts may be selected, based on the various possible connections between the electrode contacts in the tripolar electrode 10.

In operation, a microstimulator 300 is first inserted into the monopolar adapter chamber 212 through the adapter opening such that the anode contact 301 of the microstimulator 300 is abutted against the inside end of the indifferent contact 201 within the adapter chamber 212. The microstimulator 300 is inserted through sealing rings 207 and 208 inside the monopolar adapter chamber 212. The sealing rings 207 and 208 can be sized so that a microstimulator 300 can fit easily through each ring. A clearance space between the microstimulator and the chamber wall 212 permits the microstimulator to be easily placed inside chamber 212 without sticking. After the microstimulator is placed in the adapter chamber 212, a connector 40 (or connector 45) may be inserted through the adapter opening. The end 210 of the monopolar adapter 200 may have a slightly larger circumference compared to the adapter mid-portion 203. The lip 213 at the adapter end allows a clinician to grasp the adapter and pull it towards the connector 40 to snap the circular flange 56 of the connector 40 into the complementary circular recess 211 in the monopolar adapter 200. The circular lip 213, placed at the adapter opening, can also be grasped when inserting the microstimulator into the adapter chamber 212.

By pulling the adapter end 210, the length of the adapter from the adapter opening end to the opposite end is stretched. After the flange 56 is snapped into the complementary recess 211, the adapter wall, which is preferably an elastic material such as silicone or polyurethane, is under elastic tension and the microstimulator inside the adapter chamber 212 is under compression. As a consequence, the microstimulator's cathode contact 304 is urged against the connector contact 58, thereby ensuring good electrical contact. At the same time, the microstimulator's indifferent contact 302 at end 301 is urged against the adapter's indifferent electrode 201, thereby ensuring good electrical contact.

After the microstimulator is inserted into the monopolar adapter chamber 212 and the connector 40 is inserted, so that the circular flange 56 fits snugly into the complementary shaped circular recess 211, a locking feature helps to lock the connector 40 to the adapter 200 and to create a water tight seal. To achieve this seal, a slidable locking (or sliding) ring 204 is advanced towards the adapter opening at the lip 213. Because the adapter portion between lip 213 and portion 210 has a slightly large outer circumference than the adapter mid-portion 203, advancing the sliding ring 204 towards the end of the adapter compresses that section of the adapter which is over the recess 211. The compression thus achieved helps to lock the flange 56 into the adapter recess 211 and form a water-tight seal. Another slidable locking (sliding) ring 202 can be used on the other end of the adapter, which portion also has a slightly larger exterior circumference compared to the mid-portion 203 of the adapter. Advancing the sliding ring towards the adapter end forms a water-tight seal between the silicone or polyurethane insulation portion of the adapter and the indifferent adapter electrode contact 201 over the threaded portion 220.

Figure 6:
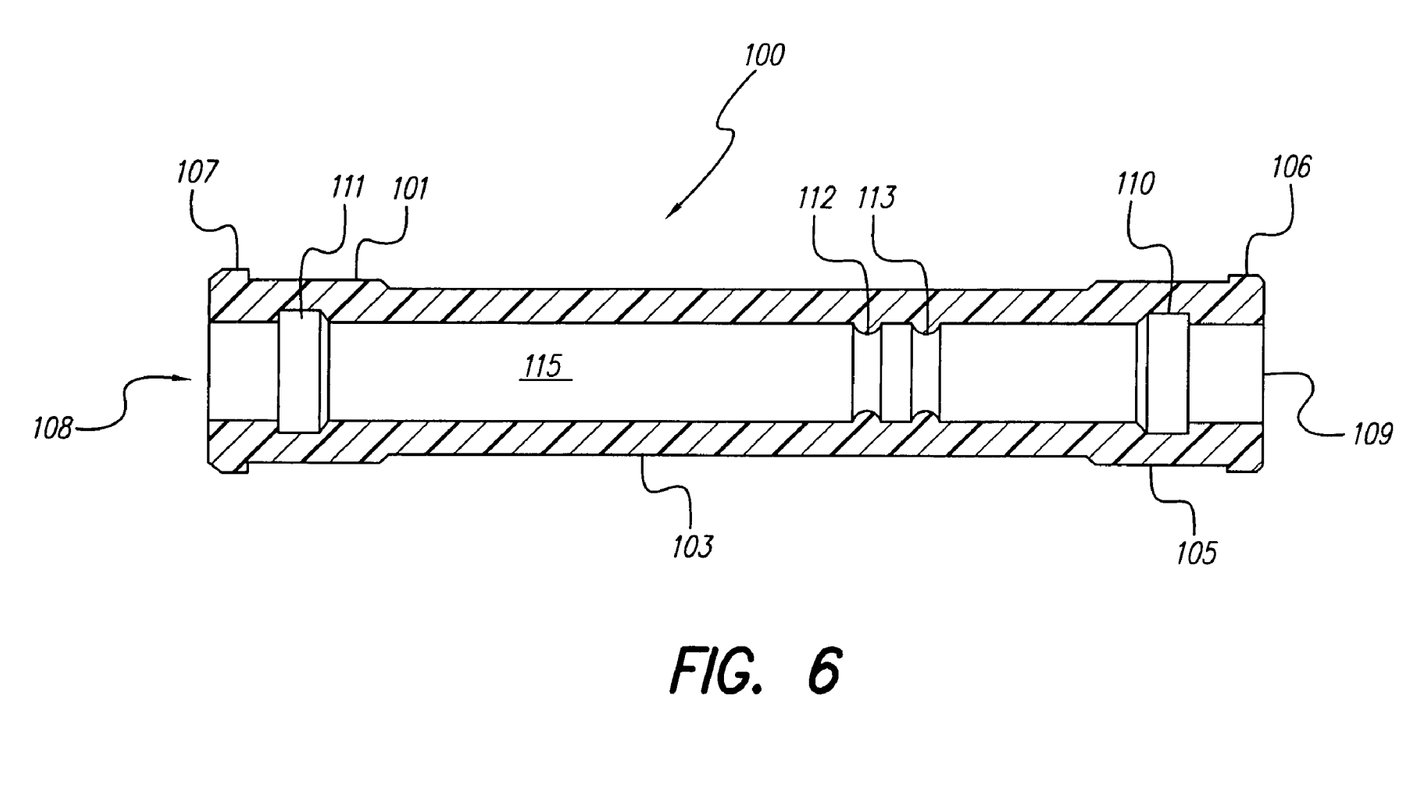
FIG. 6 shows, in accordance with the present invention, a bipolar adapter.

FIG. 6 shows, in accordance with the present invention, a cross-sectional view of a bipolar adapter 100 having a first adapter opening 108 and a second adapter opening 109 which are located at the first adapter end 101 and the second adapter end 105, respectively. The bipolar adapter has circular recesses 110 and 111 within adapter chamber 115, which recesses are complementary in dimension and shape to the circular locking flange 56 on the lead extension 40 (or extension 45). The bipolar adapter 100 also includes end lips 106 and 107 which may be used to help grasp the adapter 100 during insertion of the microstimulator 300 into the adapter chamber 115 or when the extension lead connector 40 or 45 is inserted into either the first opening 108 or second opening 109. In addition, the inside of the bipolar adapter chamber 115 includes sealing rings 112 and 113. The end portions 101 and 105 of the adapter 100 are slightly larger in circumference than the adapter's mid-portion 103.

Figure 7:
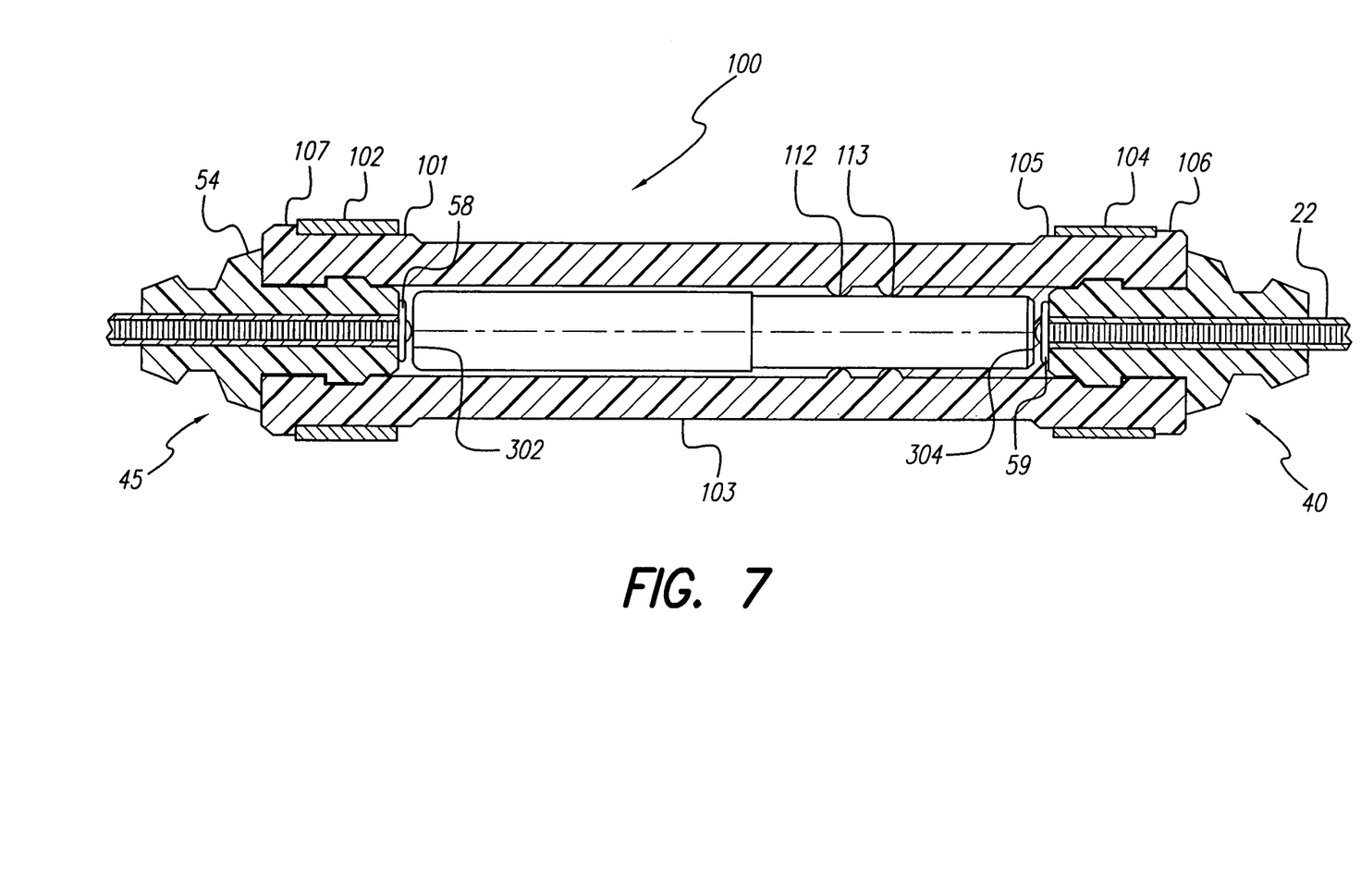
FIG. 7 shows the bipolar adapter of FIG. 6 but with the microstimulator placed into the adapter chamber and with a lead connector placed into each of the adapter chamber openings.

FIG. 7 shows a side, cross-sectional view of the bipolar adapter of FIG. 6 but with the microstimulator 300 inserted into the adapter chamber and with the extension lead connectors 45 and 40 inserted into the first and second adapter openings. The view also shows sliding ring 102 and sliding ring 104 which serve the same function as with the monopolar adapter. That is, the sliding rings serve to help form a water tight seal between the lead extension connectors 40 and 45 and the adapter body, which is preferably insulative material such as silicone or polyurethane.

Referring to FIGS. 6 and 7, the bipolar adapter 100 may also have circular end lips 107 and 106 which are circumferentially larger than end portions 101 and 105, respectively. End lips 107 and 106 may be used to grasp the adapter when the microstimulator 300 is inserted into the adapter chamber through either adapter opening 108 or 109. In addition, the lips may be used to help grasp the bipolar adapter when the connecter 40 or 45 is inserted into opening 109 or 108, thereby locking the flange 56 of the connector 40 or 45 into complementary recesses 110 or 111 of the adapter.

The circular sealing rings 112 and 113 protrude from the inside wall of the adapter chamber 115. The sealing ring or rings help center the microstimulator within adapter chamber and also prevent passage of fluid from one end of the adapter chamber to the other end and, thus, help prevent a short between the two microstimulator electrodes 302 and 304, as shown in FIG. 7.

The operation of the bipolar adapter is similar to the operation of the monopolar adapter. The microstimulator 300 is first placed into the adapter. Next, connector 40 is placed into opening 108 and connector 45 is placed into opening 109. After these steps are completed, electrode contacts 12 and 14 of the tripolar electrode 10 (FIGS. 4A, 4B and 4C) are connected to the microstimulator electrode contact facing adapter opening 109 (FIG. 6) and tripolar electrode contact 13 is connected to the microstimulator electrode contact facing adapter opening 108. Alternatively, connector 40 can be placed into adapter opening 109 and connector 45 can be placed into adapter opening 108. After the connectors 40 and 45 have been inserted into the adapter openings 108, 109, the sliding rings, 102 and 104, which are preferably made from a bio-compatible metal such as stainless steel, can be advanced to their respective ends of the adapter 100 to thereby lock the connectors 40 and 45 into place in their complementary recesses. Because the exterior diameter (or circumference) of the adapter increases slightly towards the adapter ends, sliding either ring towards an adapter end compresses that adapter end and thereby locking the inserted connector 40 or 45.

Thus, in accordance with the present invention, the system of the present invention can include at least one adapter, either monopolar or bipolar. If a monopolar adapter is used, the system includes at least one extension lead with a connector that is to be inserted into the one opening of the monopolar adapter. If a bipolar adapter is used, the system includes at least two extension leads with two connectors for insertion into the two openings in the bipolar adapter.

While the example lead extension and adapter system are illustrated as adapting a leadless microstimulator to a tripolar, semi-cuff electrode, the type of electrode is not important. It is emphasized that the adapter system of the present invention does not depend on the particular shape or configuration of the stimulating electrode selected, as the adapter system can accommodate any type of monopolar electrode (one electrode contact), a bipolar electrode (two electrode contacts), a tripolar electrode (three electrode contacts), or an electrode having greater than three electrode contacts. The latter, multi-contact electrode array may be employed as either a monopolar or bipolar electrode, with various optional connections made between the array of electrode contacts.

For example, it is possible to use the system with a monopolar electrode having a single extension lead and one lead connector 40. In such a case, a monopolar adapter 200 (FIG. 5) can be used. The microstimulator 300 is placed into the adapter chamber 212 so that the end 301 of the microstimulator's indifferent electrode contact 302 is in electrical contact with the indifferent contact 201 of the adapter 200. The lead connector 40 is inserted into opening 206 to place connector contact 59 in electrical connection with the microstimulator cathode contact 304. The tripolar electrode 10 can be used in a monopolar configuration. For example, the electrode contact 13 (FIG. 4C) may be connected and electrode contacts 12 and 14 disconnected.

A bipolar electrode configuration may be achieved using the bipolar adapter 100 and the tripolar electrode 10 in a bipolar configuration mode. For example, electrode 12 may be left unused and connection 24 may be disconnected, converting the tripolar electrode 10 into a true bipolar, semi-cuff electrode. The connections to the bipolar adapter are otherwise identical as previously described.

In summary, the present invention utilizes a leadless microstimulator having a cathode and anode electrode contacts integrated on the microstimulator body at either end, wherein the microstimulator is shaped substantially as an elongated cylinder. The present invention provides an adapter system that can be connected to a variety of electrode types via one or two extension leads without any preparatory alterations to the physical design of the leadless microstimulator.

While the invention herein disclosed has been described by means of specific embodiments and applications thereof, numerous modifications and variations could be made thereto by those skilled in the art without departing from the scope of the invention set forth in the claims.

What is claimed is:

1. A stimulation system comprising a leadless microstimulator having two stimulating electrodes attached to at least one extension lead;
    a monopolar adapter, having an inner, adapter chamber that is sized to accept placement of the microstimulator therein,
    wherein the adapter chamber has an adapter opening on one end of the adapter; and
    wherein the monopolar adapter has an indifferent electrode; and
    a connector having a contact connected to the at least one extension lead, which, in turn, is connected to the stimulating electrode,
    wherein at least part of the connector is dimensioned to be inserted into the opening of the monopolar adapter; and
    wherein the connector contact is in contact with one of the stimulating electrodes of the microstimulator.

2. The system of claim 1, wherein the indifferent electrode on the adapter is connected to a contact contained inside the adapter chamber.

3. The system of claim 1, wherein adapter chamber is substantially cylindrical.

4. The system of claim 3, further comprising:
    at least one sealing ring, which sealing ring is sized to tightly encircle the microstimulator.

5. The system of claim 4, wherein the sealing ring is integral to a adapter chamber wall and which sealing ring is made from the same material as the adapter chamber wall.

6. The system of claim 1, wherein a body of the adapter is predominantly made from a compressible, insulating material.

7. The system of claim 1, wherein the adapter has an exterior shape that is substantially cylindrical.

8. The system of claim 1, wherein the adapter chamber near the adapter opening includes a circular recess and the connector connected to the at least one extension lead has a complementary flange which fits the circular recess.

9. The system of claim 8, wherein the adapter further includes a sliding ring that encircles an exterior of the adapter and which ring is configured and dimensioned to permit it to slide over a length of the adapter,
wherein the adapter, near the opening end, has an outer circumference that is slightly larger than a mid-portion of the adapter,
whereby, when the sliding ring is advanced towards the adapter opening the ring compresses the adapter wall and thereby locks the complementary flange into the circular recess.

10. The system of claim 9, wherein the sliding ring is a biocompatible metal.

11. A stimulation system comprising for connecting a leadless, microstimulator having a stimulating electrode and having at least a first and second extension leads;
a bipolar adapter, having a first and second ends, and an inner, adapter chamber that is sized to accept placement of the microstimulator therein,
wherein the adapter chamber has a first adapter opening on first adapter end and a second adapter opening on the second adapter end;
a first connector connected to the first extension lead, wherein at least part of the first connector is dimensioned to be insertable into the first adapter opening; and
a second connector connected to the second extension lead,
wherein at least part of the second connector is dimensioned to be insertable into the second adapter opening.

12. The system of claim 11, wherein the chamber length is sized such that when the microstimulator is inserted into the bipolar adapter chamber and when the first connector is inserted into the first opening of the adapter chamber and the second connector is inserted into the second opening of the adapter chamber, the adapter chamber wall is under elastic tension in the lengthwise chamber direction.

13. The system of claim 11, wherein the bipolar adapter chamber is substantially cylindrical.

14. The system of claim 13, further comprising:
at least one sealing ring, which ring is sized to tightly encircle the microstimulator.

15. The system of claim 14, wherein the sealing ring is integral to a bipolar adapter chamber wall and which sealing ring is made from the same material as the bipolar adapter chamber wall.

16. The system of claim 11, wherein the bipolar adapter is made predominantly from an compressible, insulating material.

17. The system of claim 11, wherein adapter has an exterior shape that is substantially cylindrical.

18. The system of claim 17, wherein the bipolar adapter chamber has a first circular recess near the first adapter opening and a second circular recess near the second adapter opening and wherein the first connector has a flange which fits into the first circular recess and the second connector has a flange that fits into the second circular recess.

19. The system of claim 18, wherein the adapter further includes first and second sliding rings that encircle an exterior of the adapter and each sliding ring is configured and dimensioned to permit each ring to slide over a length of the adapter,
wherein the adapter, near the first opening end, has an outer circumference that is slightly larger than the mid-portion of the adapter; and
wherein the adapter, near the second opening, has an outer circumference that is slightly larger than the mid-portion of the adapter,
whereby when a sliding ring is advanced towards an opening the ring squeezes and compresses the adapter wall and the complementary flange is locked into the circular recess.

20. The system of claim 19, wherein the first and second sliding rings are each made from a biocompatible metal.

* * * * *